US00PP10445P

United States Patent [19]

Lemon

[11] Patent Number: Plant 10,445

[45] Date of Patent: Jun. 9, 1998

[54] VARIETY OF GERANIUM PLANT NAMED 'ROYAL PINK'

[75] Inventor: David Lemon, Lompoc, Calif.

[73] Assignee: John Bodger & Sons Company, So. El Monte, Calif.

[21] Appl. No.: 724,679

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 6,030 9/1987 Kirmann ..... Plt./87.12

*Primary Examiner*—Howard J. Locker

*Attorney, Agent, or Firm*—Fulwider Patton Lee & Utecht, LLP

[57] ABSTRACT

The cultivar is characterized by its medium green foliage and deep pink bloom with dark red eyes. Royal pink brings a true pink color to the Royalty series. Its relatively strong growth habit, habit, quick rooting time and continuous flowering provide for superb cuttings and also for quick recovery following wet weather conditions. The blooms exhibit good post-harvest quality.

1 Drawing Sheet

BACKGROUND OF THE NEW PLANT

The present invention comprises a new and distinct cultivar of *Pelargonium×domesticum* known by the varietal name Royal Pink (Oglevee No. 711, Bodger No. 2 PD 17-7). The new variety was discovered in a selective breeding program by David Lemon at Bodger Seeds, Ltd., Lompoc, Calif. The new variety is a selection from the crossing of Prince (U.S. Plant Pat. No. 8,090) which is characterized by deep green foliage and a medium purple flower, with Mutter Tag (Bodger No. 8 PD 24-1 unpatented) which has red flowers as distinguished from the claimed cultivar which has medium green foliage with a deep pink bloom having dark red eyes.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pennsylvania, using full light, 60° Fahrenheit night temperature, 68° Fahrenheit day temperature, and grown in a soilless media of constant fertilizer 150–200 parts per million of nitrogen and potassium has a response time of fourteen weeks from the rooted cutting to a flowering plant in a 6 inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Apr. 25, 1996 under full light and greenhouse, and colorings were taken indoors under 200–220 foot candles of fluorescent cool white light using The R.H.S. Colour Chart of The Royal Horticultural Society of London.

The Plant

Classification:
- *Botanical.*—*Pelargonium×domesticum.*
- *Commercial.*—Regal Geranium Royal Pink.

Form: Upright mound.
- *Height.*—25.0–28.0 cm above media.
- *Growth.*—Vigorous.
- *Strength.*—Fast rooting, good postharvest performance.

Foliage: Stalked leaf attachment.

Leaves:
- *Size.*—5.5–7.5 cm.
- *Shape.*—Depressed ovate, truncate base.
- *Margin.*—Serratedly lobed.
- *Texture.*—Leathery, slightly pubescent.
- *Color.*—Top: Green group 137B. Bottom: Green group 137C. Zone: None.
- *Ribs and veins.*—Palmate venation: Color: Yellow/green group 147C.

Petioles:
- *Length.*—6.0–7.5 cm.
- *Color.*—Yellow/green group 146B.

Stem:
- *Color.*—Yellow/green group 146C.
- *Internodes.*—1.5–3.0 cm.

The Bud (Umbel)

Shape: Elliptical.

Size: 3.5–4.0 cm across; color just showing.

Inflorescence

Blooming habit: Continuous, free flowering.

Borne: Umbel; floret on pedicel; pedicel on peduncle.

Closed florets:
- *Bud size.*—1.5–2.0 cm in length, 0.6–1.0 cm in width.
- *Size.*—Fully open bloom 8.5–9.5 cm across.

Open florets:
- *Form.*—Cupped.

*Color.*—Top: Red-purple group 58D. Bottom: Red-purple group 62D. Eye: Upper two petals Red group 53A; Lower three petals very faint Red group 46C.
*Petals.*—Five.
*Size.*—4.5–5.5 cm across.
*Texture and Appearance.*—Satiny; appearance from a distance is bloom of deep pink with a dark red eye above medium green foliage.

Petaloids:
*Quantity.*—None.

Pedicel:
*Length.*—1.8–2.0 cm.
*Color.*—Yellow-Green group 146C.

Peduncle:
*Length.*—4.5–5.5 cm.
*Color.*—Yellow-green group 146A.

Persistence:
*Disease Resistance.*—Not known.
*Lasting Quality.*—Unknown.

Reproductive Organs

Stamens:
*Anthers.*—2.0–3.0 mm in length.
*Filaments.*—Length: 1.0–1.4cm. Color: White.
*Pollen.*—Golden brown.

Pistils:
*Number.*—One.
*Length.*—1.6–2.0 cm.
*Stigma.*—Color: Red-purple group 60C; 5–7 parted.
*Style.*—Length 7–8 mm.

Ovaries:
*Color.*—Pale Green, Pubescent; Superior.
*Length.*—5–6 mm.

Fruit: None.

General Characteristics

Rapture brings a true pink color to the Royalty series. The Royalty Series is an easy to grow plant characterized by vigorous upright growth habit, continuous flowering and abundant flowers. Florets are much larger, and cutting production, rooting time and lasting quality are improved over the current Royalty varieties.

I claim:

1. A new and distinct variety of Geranium plant, substantially as shown and described.

* * * * *

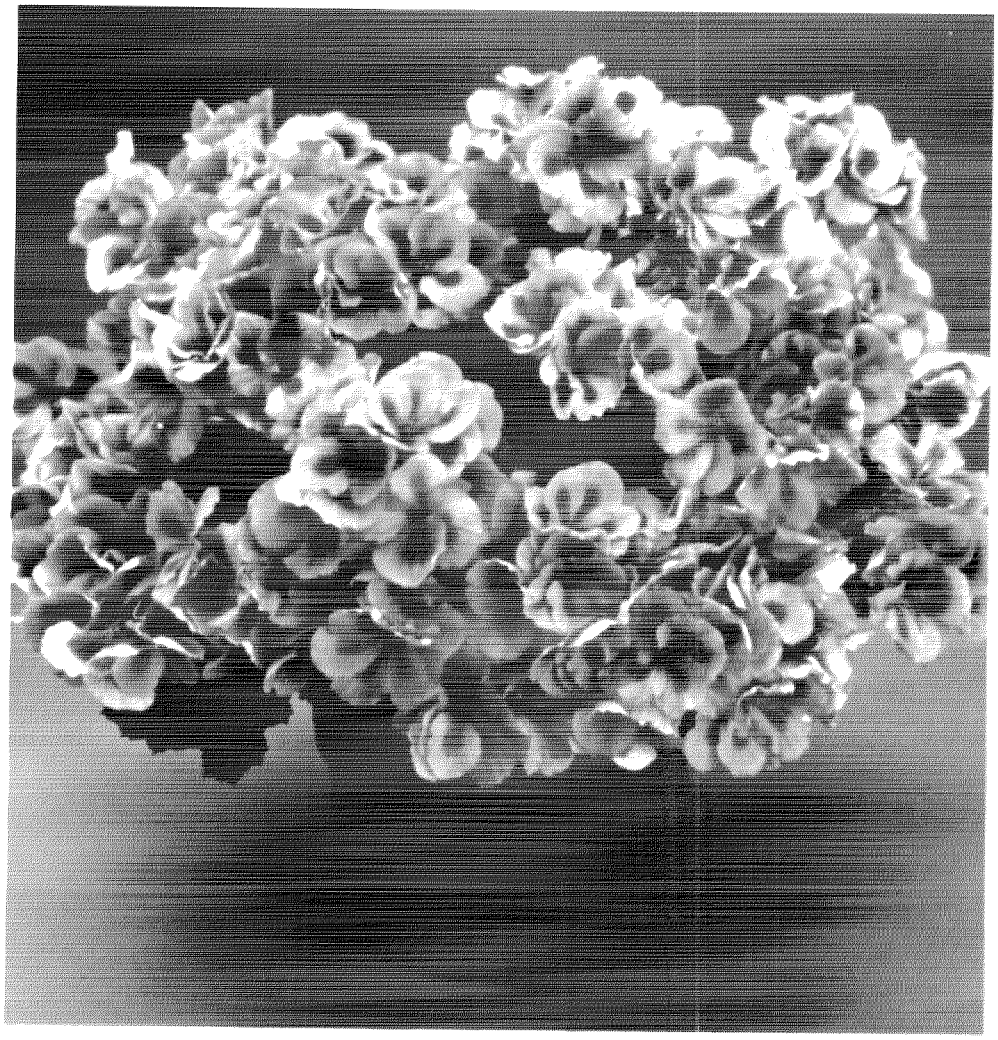

UNITED STATES PATENT AND TRADEMARK OFFICE

CERTIFICATE OF CORRECTION

PATENT NO. : PP10,445

DATED : June 9, 1998

INVENTOR(S) : David Lemon

It is certified that error appears in the above-identified patent and that said Letters Patent is hereby corrected as shown below:

Column 4, Line 13, delete "Rapture" and insert -- Royal Pink--.

Signed and Sealed this

Second Day of February, 1999

*Attest:*

*Attesting Officer*

*Acting Commissioner of Patents and Trademarks*